United States Patent [19]

Ju

[11] Patent Number: 4,861,589

[45] Date of Patent: Aug. 29, 1989

[54] METHOD FOR THERAPEUTICALLY TREATING ABNORMAL CELLS EXPRESSING A MAJOR HISTOCOMPATIBILITY COMPLEX CLASS II ANTIGEN USING CYTOLYTIC INDUCER T4 CELLS

[75] Inventor: Shyr-Te Ju, Winchester, Mass.

[73] Assignee: Trustees of Boston University, Boston, Mass.

[21] Appl. No.: 28,848

[22] Filed: Mar. 23, 1987

[51] Int. Cl.$^4$ .................... A61K 45/05; A61K 35/26; C12N 5/00; C12N 5/02

[52] U.S. Cl. .................... 424/93; 530/351; 530/395; 530/806; 530/808; 530/828; 435/240.2; 435/240.1; 435/243; 435/244; 424/85.1; 424/85.8; 935/101; 935/105; 935/107; 935/109

[58] Field of Search ............. 424/88, 85, 86, 92; 435/172.2, 241; 935/107; 514/21; 530/806, 828, 808, 395, 350, 351

[56] References Cited

U.S. PATENT DOCUMENTS

| | | | |
|---|---|---|---|
| 4,681,760 | 7/1987 | Fathman | 424/91 |
| 4,690,915 | 9/1987 | Rosenberg | 514/2 |
| 4,695,459 | 9/1987 | Steinman et al. | 424/95 |

OTHER PUBLICATIONS

Zier, J. Imm. Methods, 84, 73–84 (1985).
Clayberger et al, J. Exp. Med., 157, 1906–19 (1983).
Damle et al, J. Immunol., 132(2), 649–650 (1984).
Chizzolini et al, J. Immunol., 137(3), 1022–8 (1986) (Aug.).
Ettinghausen et al, J. Immunol., 135(5), 3623–35 (1985).
DeKruyff et al, J. Immunol., 135(4), 2243–8 (1985).
Reinherz et al, J. Immunol., 126(1), 67–70 (1981).
Damle et al, J. Exp. Med., 158, 159–73 (1983).
Schmitt et al, Eur. J. Immunol., 12, 849–54, (1982).
Umetsu et al, Eur. J. Immunol., 15, 356–61, (1985).
Puri et al, Eur. J. Immunol., 15, 362–8, (1985).
Blue et al, PNAS (USA), 82, 8178–82, (1985).
DeKruyff et al, J. Immunol., 136(2), 446–51, (1985).
Damle et al, J. Immunol., 133(3), 1235–40, (1984).
Tite et al, J. Immunol., 135(1), 25–33, (1985).
Dialynas et al, J. Immunol., 131(5), (1983).
Rosenberg et al, Science, 233, 1318–22, (1986).
Ettinghausen et al, J. Immunol., 135(2), 1488–97, (1985).
Ju et al, J. Immunol, 134(6), 3722–30, (1985).
"Cellular Immunology", vol. 2, Weir et al., (Eds.), pp. 71.1–71.7 and 75.1–75.7, (1986).
Umetsu et al., J. Immunol. 140:4211–4216 (1988).
Lanzavecchia et al., J. Exp. Med. 167:345–352 (1988).

*Primary Examiner*—Margaret Moskowitz
*Assistant Examiner*—Jeff P. Kushan
*Attorney, Agent, or Firm*—David Prashker

[57] ABSTRACT

The present invention provides a lymphocyte-mediated immunotherapy for the treatment of human or animal subjects afflicted with abnormal or tumor cells which express a MHC Class II antigen on their surface. The method utilizes inducer T-cell clones or lines having a demonstrable specificity for an identifiable antigen. These T-cells are activated in-vivo to express cytolytic and therapeutic activity against the abnormal or tumor cells in the subject.

7 Claims, 2 Drawing Sheets

FIG. 2
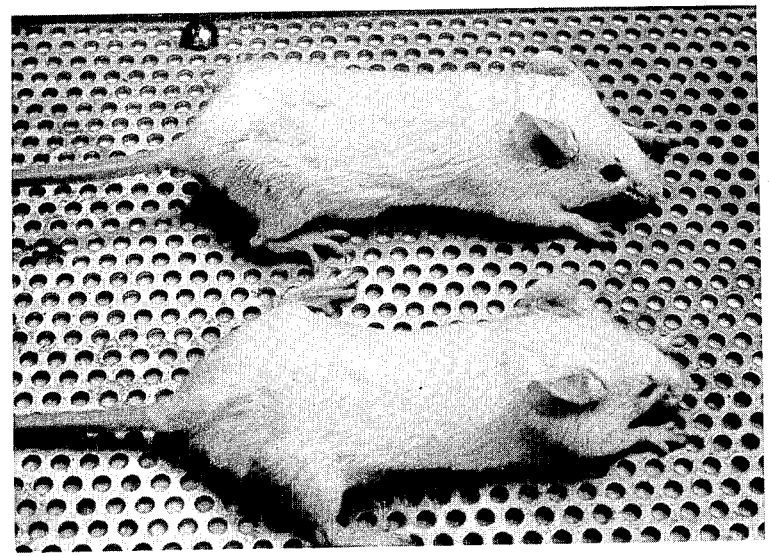
FIG. 2A
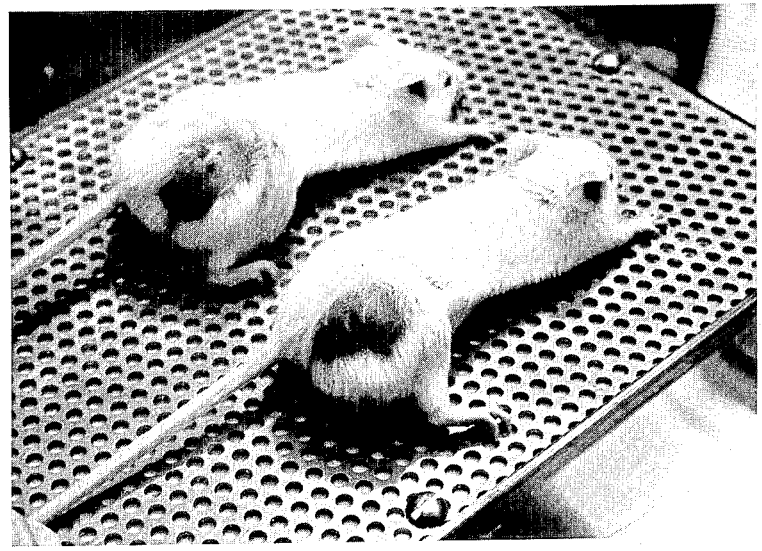
FIG. 2B

METHOD FOR THERAPEUTICALLY TREATING ABNORMAL CELLS EXPRESSING A MAJOR HISTOCOMPATIBILITY COMPLEX CLASS II ANTIGEN USING CYTOLYTIC INDUCER T4 CELLS

FIELD OF THE INVENTION

The present invention is concerned with therapeutic methods for treating tumors in a living subject and is particularly directed to methods of activating inducer T-cell clones in-vivo to achieve a therapeutic effect against tumor cells in a subject.

BACKGROUND OF THE INVENTION

The discovery of the human major histocompatibility complex (hereinafter "MHC") dates from the mid-1950's, when leukoagglutinating antibodies were first found in the sera of multiply transfused patients in a pattern that suggested the antisera were detecting alloantigens, antigens present on the cells of some individuals of a given species which are products of a polymorphic genetic locus. The role of these antigens in determining the success of tissue and organ transplants was soon appreciated and provided the initial studies of genes that determine human leukocyte antigens (hereinafter "HLA").

The HLA system is extremely polymorphic, having multiple different alleles at each known genetic locus. Based on their tissue distribution and structure, HLA antigens have been divided into two broad classes: Class I antigens which include the HLA-A, -B, and -C antigens found on virtually every human cell and which have counterparts in other mammalian cells including the murine system; and Class II antigens including the HLD-, DR, DQ, and DP antigens found chiefly on the surfaces of immunocompetent cells including macrophages/monocytes, activated T-lymphocytes, and B lymphocytes. Class II antigens also have counterparts in other mammalian systems such as murine mammals. The presence of these Class I and Class II antigenic molecules plays a major role in the functional heterogeneity of peripheral T-cells.

The different regulatory and effector functions of T-cells are mediated by different subpopulations of cells which can be distinguished by differences in their phenotypes and antigenic determinants (identifiable by different monoclonal antibodies). This has led to the typing of T cell functional subsets in accordance with the expression of specific surface molecules which are commonly designated by the letter "T" followed by a number. Based on functional differences between T4 and T8 cells, the peripheral blood T-cells can be broadly divided into two populations: one population constituting approximately 65% of peripheral blood T-cells is T4+; the other constituting approximately 35% of all peripheral blood T-cells is T8+. The T8+ cell may be activated to become a cytolytic T lymphocyte (hereinafter "CTL cell") which functions as a cytotoxic effector cell and plays an important role in the hosts' defense against foreign bodies. In combination with natural killer cells (hereinafter "NK cells") and lymphokine activated killer cells (hereinafter "LAK cells"), these cells respond to protect the body against invasion by foreign cells and substances. The role of the T4+ cell has been traditionally viewed as an inducer cell for the activation of other T-cell subpopulations. This role is achieved in combination with an accessory cell or antigen presenting cell (hereinafter "APC") which bears Class II MHC molecules on its surface and is able to take up and process an identifiable antigen. The antigen presented by an APC bearing Class II molecules activates specific T4+ cells. The activated T4+ cells in turn secrete a variety of lymphokines to initiate the effector and cytolytic functions of other T-cell lymphocytes. It is noteworthy that with the increasing use of lymphocyte-mediated immunotherapies including those directed against tumors, all such immunotherapies utilize only those activated lymphocytes equipped with cytolytic effector function such as CTL cells, NK cells, and LAK cells. T-cells of the inducer phenotype are traditionally viewed as lacking the necessary cytolytic activity and therefore have not been considered useful for treatment of tumors as immunotherapeutic lymphocytes.

The human system of multiple T-cell subpopulations has a direct counterpart in the murine system. There are two major functional subsets of T-lymphocytes in the murine system [Cantor and Boyse, J. Exp. Med. 141:1376 (1975)]. The L3T4+ subset of T-lymphocytes has inducer or helper functions and is generally activated by APCs that bear exogenous antigen and express Class II molecules (Ia) of the MHC [Dialynas et al., Immunol. Rev. 74:29 (1983)]. This subset is equivalent to the T4+ lymphocyte subpopulation in humans. The second major T-cell subset expresses Lyt-2 determinants and possesses either suppressor or cytolytic functions. These are equivalent to T8+ lymphocytes in humans. When activated, Lyt-2 cells become cytolytic T-lymphocytes (CTL cells) which generally lack the L3T4+ antigenic marker and which recognize Class I molecules of the MHC [Zinkernagel and Doherty, J. Exp. Med. 141:1427 (1975)].

As in the human system, it has been traditionally viewed that L3T4+ inducer T cells help initiate the effector functions of other T-lymphocytes, but do not demonstrate any cytolytic effect themselves. Very recently however, several investigators observed an effector function for selected L3T4+, antigen-specific, Ia-restricted T-cell clones [Tites et al., J. Immunol. 135:25 (1985); Nakamura et al., J. Immunol. 136:44–47 (1986); Lukacher et al., J. Exp. Med. 162:171 (1985)]. These investigations comprised in-vitro experiments in which selected L3T4+ clones appeared to be cytolytic in short-term (less than 6 hours) chromium release assays for Ia-bearing B-cell hybridoma targets in the presence of antigen. The primary thrust of each report dealt with the specificity and the killing mechanism(s) for the observed cytotoxicity. To date, therefore, there is little knowledge or appreciation as to: whether inducer T-cells generally in murine and human systems are able to express cytolytic effector function; whether all major types of antigen presenting cells are sensitive to such cytolytic activity; whether such cytolytic activity can be maximally expressed and, if so, under what conditions; and whether such inducer T-cell cytolytic activity can be utilized in-vivo for any therapeutic purpose.

SUMMARY OF THE INVENTION

The present invention is a method for treating a subject afflicted with tumor cells expressing a major histocompatibility complex Class II antigen either constitutively or inductively, comprising the steps of administering a plurality of antigen specific inducer T-cell lymphocytes to the subject; introducing an identifiable specific antigen to the subject; and waiting a predetermined time period for the inducer T-cell lymphocytes to become activated in-vivo and to express cytolytic activity against the tumor cells in the subject.

The inducer T-cell lymphocytes are preferrably prepared and maintained as a T cell clone or line of known antigenic specificity and surface phenotype. The methodology is deemed useful for therapeutic treatment of neoplasms whose cells bear a MHC Class II antigen on their surface.

DETAILED DESCRIPTION OF THE DRAWING

Figure 1:
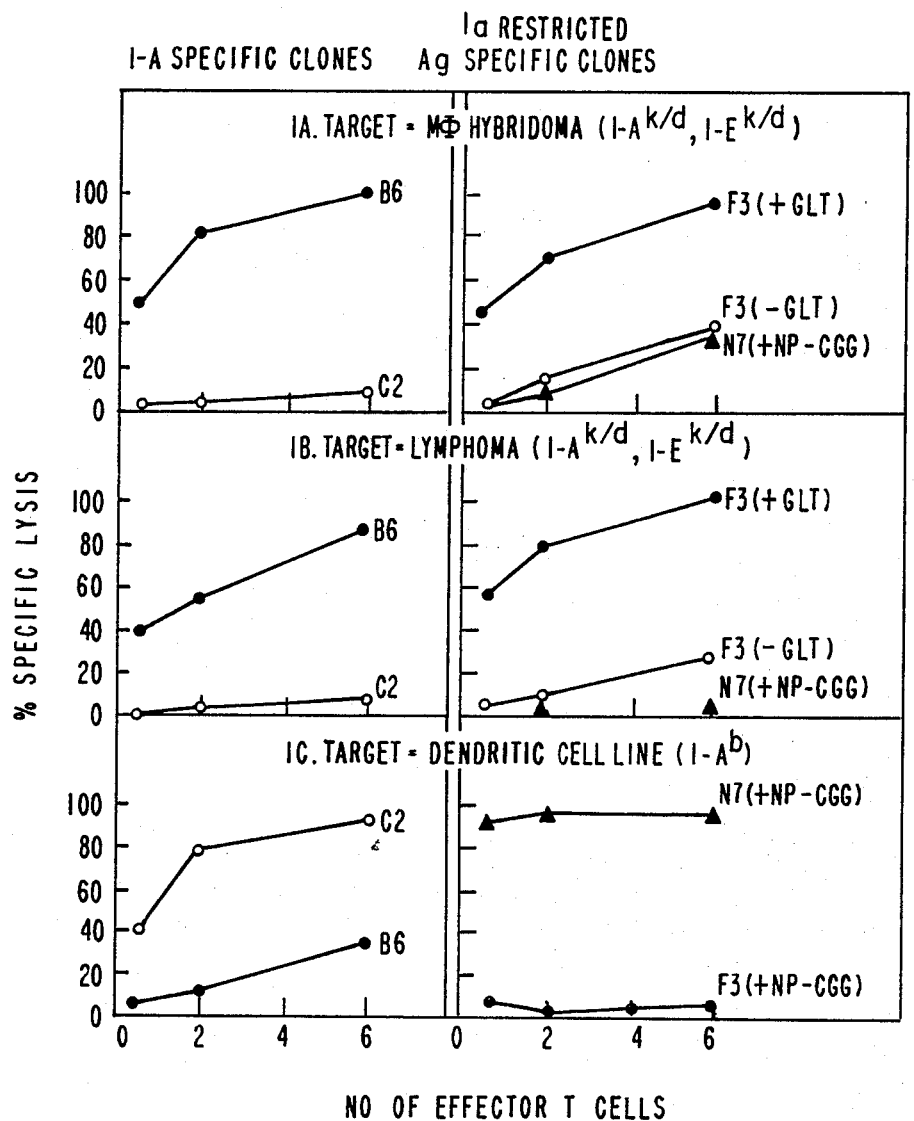

The present invention may be more easily and completely understood when taken in conjunction with the accompanying drawing, in which:

FIGS. 1a-1c are a series of graphs illustrating the specific lysis of different antigen presenting cells by a variety of different L3T4+ inducer T-cell clones; and FIGS. 2a and 2b are photographs illustrating the growth and inhibition of growth of a tumor in mice receiving inducer T-cells in the absence or presence of specific antigen respectively.

DETAILED DESCRIPTION OF THE PREFERRED EMBODIMENTS

The present invention is a method for treating abnormal cells and tissues, such as tumor cells, in a living human or animal subject utilizing a pool of antigen specific inducer T-cell lymphocytes which, in combination with an introduced specific antigen become activated in-vivo to express cytolytic and therapeutic activity against the abnormal (tumor) cells in the body. Inducer T-cell lymphocytes are recognized as T4+ lymphocytes in humans and as L3T4+ lymhocytes in murine systems. The generally accepted view in this art is that T cells of the inducer phenotype are unable to demonstrate any cytolytic activity themselves and instead function to help activate other kinds of T cells (such as T8+ phenotype lymphocytes) to become cytolytic T-lymphocytes. In contradistinction, the present invention utilizes and relies upon the ability of antigen specific inducer T-cells to become activated in the presence of an antigen presenting cell (hereinafter "APC") in combination with an introduced specific antigen. Once activated in this manner, inducer T-cell lymphocytes express strong cytolytic effector function in-vivo. Under in-vitro experimental conditions, the killing activity is apparent 9 hours after contact between the inducer T-cell clones and the antigen-bearing APC while a maximum cytolytic effect is obtained at approximately 20 hours duration. In many instances, it is preferred that additional introductions of specific antigen or interleukin-2 be administered in order to continue and prolong the proliferation, activated state, and cytolytic activity of the inducer T-cell lymphocytes in-vivo.

The present invention offers several unique features and advantages to the user as a therapeutic treatment which were not known nor previously available in this art. Initially, it is unique to the present methodology that inducer T-cell lymphocytes can be activated in-vivo to express cytolytic and therapeutic activity in-vivo. Second, the inducer T-cell lymphocytes may be grown and maintained indefinitely as clones or lines, pure cell cultures of known antigenic specificity and phenotype; and which may then be administered to the subject at a time and by a route of the user's own choosing. Third, activation of the administered inducer T-cell lymphocytes occurs in-vivo with the introduction of an identifiable specific antigen which is captured by the abnormal tumor APC and is presented in combination with the MHC Class II antigen of the APC to activate the administered T-cell lymphocytes. This allows the user another degree of control by individual selection of the specific antigen to be employed as well as the timing and route of introduction to the subject. Fourth, once activated, the inducer T-cell lymphocytes exhibits cytolytic activity in what is believed to be a non-specific mode; the activated T-cell cognatively recognizes the presence of the APC as the adjacently positioned cell and therefore directs its cytolytic action primarily against those cells in the immediate area—that is, the tumor cells themselves. In this manner, the cytolytic activity can be directed with reasonable precision at a known and localized site. Fifth, and perhaps most important, while the cytolytic activity of the activated inducer T-cell lymphocyte is comparably small in comparison to that demonstrated by CTL cells, NK cells, and LAK cells, a unique advantage and strength of the activated helper T-cell lymphocytes is their ability to proliferate concurrent with their demonstrated ability to kill the antigen-presenting cells. This ability to proliferate concurrent with cytolytic activity greatly enhances the overall killing activity of inducer T-cell lymphocytes; and provides the heretofore unavailable ability to prolong the cytolytic effect at therapeutically effective rates for weeks or months. Proliferation of cytolytic T-cells and prolongation of cytolytic activity thus provides a therapeutic treatment which will greatly inhibit the growth of a tumor and, in some instances, will completely eradicate the tumor using a preset regimen.

In order to completely and clearly understand and appreciate the therapeutic method comprising the present invention, each of the reactants employed in the manipulative steps will be described in detail. While many of the specific examples pertain to cells and conditions in murine systems, it will be expressly understood that human equivalents and counterparts are well known and described in the pertinent literature; and that human derived T-cell lymphocytes, T-cell clones, and abnormal tumor cells expressing a MHC Class II antigen (constitutively or inductively) are readily identifiable and useful.

The Antigen Specific, Inducer T-Cell Lymphocytes

Inducer T-cell lymphocytes are a subpopulation of T-cells identifiable by phenotype using the OKT4 (or Leu3) monoclonal antibody for human cells and the L3T4 antibody (GK1.5) for murine derived cells. The analytical techniques used to identify, isolate, and maintain inducer T-cells as clones or lines in-vitro are conventionally known and are well established in this art. For this reason, such techniques need not and will not be described in detail herein. The reader is directed to the following publications for specific descriptions and details regarding similarities between T-cells subpopulations in human and murine systems; for specific protocols to establish and maintain clones of inducer T-cell lymphocytes; and for information regarding the specificities and phenotypes of T-cell lymphocytes in general: Meuer et al., *Proc. Nat. Acad. Sci. USA* 79:4395 (1982); Reinherz et al., *Cell* 19:821(1980); Reinherz et al., *Immunol. Today* 4:5 (1983); Thomas et al., *J. Clin. Immunol.* 2:8S (1982); Webb et al., *Ann. Rev. Immunol.* 1:423 (1983); Regulatory *T Lymphocytes*, Pernis & Volgel, editors, Academic Press, 1980; DeKruyff et al., *J.*

*Immunol.* 136:446 (1986); Clayberger et al., *J. Exp. Med.* 157:1906 (1983); Friedman et al., *J. Exp. Med.* 161:785 (1985); Rao et al., *Immunogenetics* 17:147 (1983).

To be useful in the methodology of the present invention, the isolated inducer T-cell lymphocytes must bear receptor sites for an identifiable specific antigen on their cell surfaces. Methods for verifying and confirming the presence of receptor sites for a specific antigen within an isolated T4+ or L3T4+ lymphocyte subpopulation are conventionally known and well established in the art. Once such T4+ and L3T4+ antigen specific lymphocytes have been isolated and verified as to antigenic specificity, such T-cell subpopulations can be stimulated in-vitro, cloned, and expanded acccording to established protocols. Clones or lines of such antigen specific inducer T-cell subpopulations are most preferred for use in the therapeutic methods. Illustrative of useful, antigen specific inducer T-cell clones are those derived from the murine system which are utilized to demonstrate the various aspects of the present invention in the experiments which follow hereinafter. It is expected that antigen specific, human derived clones of inducer T-cell lymphocytes will be similarly prepared and maintained for use.

For purposes of the present invention, the particulars of the origin, antigenic specificity, and surface phenotypes of the inducer T-cell lymphocytes, whether or not maintained as clones, are not controlling so long as no severe adverse body reactions are produced as a result of administration to the subject. Clearly, it is expected that human derived T-cell lymphocytes will be administered to human subjects and animal derived T-cell lymphocytes will be administered to the appropriate animal subject. Similarly, the route of administration is not of particular interest so long as the pool of inducer T-cells are administered to the subject in an intact viable form, without injury to the T-cells themselves; it is expected that the cells will be administered using a fluid carrier such as physiological saline or a 5% dextrose solution. A preferred route of administration is thus, intravenous or intraperitoneal injection in the conventionally known manner. Under individual circumstances and needs, localized injection cutaneously, subcutaneously, or intradermally is equally useful.

The Introduced Specific Antigen

A requisite part of the present methodology is the introduction of an identifiable, specific antigen to the subject in a manner that will permit delivery of the specific antigen to the site of the tumor or other abnormal cell. An exogenous foreign antigen is preferred. Particularly desirable exogenous specific antigens are those which have been historically used for protection against infectious diseases in the form of vaccines and/or antitoxins. A representative list of useful exogenous antigens now available in purified form include diphteria toxin antigens (*B. pertussis*); purified protein derivative (ppD); polio virus antigens; and the like. Because of such public health vaccinations, most or all humans in the Western world possess specific T4+ lymphocytes in their blood that are reactive to these exogenous antigens. These specific T4+ lymphocytes can be stimulated in-vitro, cloned, and expanded according to established protocols. The clones, preferably, are then maintained indefinitely for therapeutic purposes. Most clones of T4+ cells recognize a peptide fragment of the specific antigens. Such peptide fragments can be synthesized chemically and used in place of original antigens to reduce unwanted detrimental responses to the host such as antibody formation and immediate hypersensitivity. Both the original antigen and the synthesized peptide fragments conventionally prepared may be utilized as the host-introduced specific antigen for therapeutic purposes.

The specific composition, formula, method of preparation, purity, and route of administration for introduction of the exogenous identifiable antigen is inconsequential so long as the means of introduction cause the exogenous antigen to become localized at the site of the tumor or other abnormal cells in the subject.

Tumor Or Abnormal Cells

It is a requirement of the present invention that the tumor or other abnormal cells in the subject which are to be therapeutically treated phenotypically demonstrate (constitutively or inductively) the presence of a MHC Class II antigen on their cell surfaces. In humans, the MHC Class II antigens are the alleles comprising HLA-DR, DQ, and DP [Bach, F. H., *Immunol. Today* 6:84–94 (1985); Figuera and Klein, *Immunol. Today* 7:78–81 (1986)]. The reader is directed to additional specific texts describing and differentiating between each of the markers in the Class II antigen complex [*Immunological Review*, Moller G. (editor), Volume 70, 1983; *Tissue Antigens*, HLAN Nomenclature Committee, Volume 16, 1980; *Manual Of Tissue Typing Techniques*, Ray, J. G. (editor), NIH Publication Number 80-545, 1979]. In murine systems, the counterpart MHC Class II antigens are the Ia alloantigens including the I-A and I-E antigens.

MHC Class II antigens are generally associated with the cells of the immune system such as macrophages/monocytes; some subpopulations of activated T lymphocytes; dendritic cells (spleen); Kuppffer's cells (liver); Langerhans' cells (skin); epithelial cells (thymus and mammary gland); and particularly B lymphocytes. Many cells with no known immune functions also express these Class II antigens. Some but not all of malignant melanoma; breast cancer; bladder cancer; kidney cancer; ovarian cancer; and lung cancer express MHC Class II antigens. In addition, the majority of these cancer cell types can be induced to express high levels of these antigens even though they are not expressed constitutively [Haughton et al., *J. Exp. Med.* 160:255–269 (1984)].

Disorders of these kinds of cells which are deemed to be clinically abnormal and give rise to a diagnosable pathological state (typically as tumors of these specific tissue types) comprise the target tissues and cells for treatment by the present methodology. The underlying requirement for these tumor or other abnormal cells to be therapeutically treated is that they act as antigen-presenting cells (APCs) by: taking up the exogenous specific antigen after its introduction to the host; and present both the exogenous specific antigen and the Class II antigen such that the inducer T-cells administered to the subject make reactive contact with the tumor cell and the exogenous antigen in combination. Once activated, the inducer T-cells will proliferate and express cytolytic activity in-vivo against the tumor cells. Mechanistically therefore, the tumor or other abnormal cell expressing the MHC Class II antigen on its surface functions as an antigen-presenting cell in-vivo, thereby initiating activation of the inducer T-cell population and creating the means of the tumor cell's own destruction.

It is believed and expected that disorders of cells bearing the MHC Class II antigen may be therapeutically treated generally using the present invention. Nevertheless, for illustrative purposes only, a B cell tumor—B-lymphoma A20.2J cells—were utilized for the in-vivo experiments described hereinafter. Accordingly, so long as the tumor or other abnormal cell in the subject bears a MHC Class II antigen on the cell surface; and, in combination with an introduced specific antigen, is able to activate inducer T-cell lymphocytes in-vivo, those tumors or other abnormal cells are within the scope of the present invention.

While the therapeutic treatment for a particular individual is expected to vary with: the quantity and phenotypic characteristics of the inducer T-cell lymphocyte subpopulation; the quantity of inducer T-cell lymphocytes administered to the subject; the dosage, route of administration, and frequency of introducing one or more specific antigens; and the frequency, if any, of repeated introductions of clone and specific antigen; these considerations and details are deemed to be merely variations of personal choice or convenience to the user. It is also expected that the present methodology may be employed with other therapeuties in order to effectively treat a specific tumor or disorder in the subject. It will be recognized and appreciated, however, that none of these other considerations meaningfully detract from or limit the use of the present therapeutic method for its intended purpose.

To demonstrate the utility, effectiveness, and advantages of the present methodology, the following experimental data is presented. It will be recognized and appreciated however that the specific embodiments employed within the described experiments are merely illustrative of the subject matter as a whole comprising the present invention; and do not serve to either limit or restrict the invention to the described embodiments or formats.

Experimental Series

Illustrative of useful, antigen specific inducer T-cell clones are those derived from the murine system which are utilized to demonstrate various aspects of the present invention via experimental protocols. These murine derived clones of inducer T-cells used experimentally are maintained by periodic stimulation with appropriate antigens (generally 25–50 micrograms per milliliter (hereinafter "ug/ml") in the presence of 2500-rad irradiated syngeneic spleen cells ($5 \times 10^6$ cells/ml). These clones are expanded and maintained by the addition of Concanavalin A (hereinafter "CON A") conditioned medium containing 600 units/ml of interleukin-2 (hereinafter "IL-2").

A unit of IL-2 is defined as the volume of conditioned medium necessary to achieve 50% of the maximum proliferation of an IL-2 dependent cell line such as the CTLL line under defined conditions as follows: ten thousand CTLL cells are incubated with the samples in 200 ul final volume in a 37 C, 10% $CO_2$ incubator. After 18 hours incubation, 1 uCi of $^3$H-thymidine is added to the samples to determine the proliferation of the cells.

The conditioned medium used for the maintenance of the clones is prepared as follows: spleen cells of BALB/c mice ($5 \times 10^6$/ml) were cultured in the presence of 2.5 ug/ml of CON A for 18 hours in a 37 C, 10% $CO_2$ incubator. The IL-2 generated in the cell-free supernatant was initially depleted of CON A by binding to a DEAE cellulose column and subsequently recovered by elution with 0.44M NaCl. IL-2 containing fraction was filtered and stored at $-20$ C and diluted 25-fold with Dulbecco's Modified Eagle's Medium (hereinafter "DMEM) containing 10% fetal calf serum (hereinafter "FCS") before use.

All clones were used experimentally 10–30 days after stimulation. Viable cells were purified by centrifugation over a Ficoll-Hypaque gradient and washed with DMEM containing 10% FCS three times before use. The name, antigenic specificity, and cell surface phenotype of the T-cell clones used for experimental purposes herein are identified by Table I.

TABLE I

| CLONES | STRAIN OF ORIGIN | SPECIFICITY | CPM OF LABELED F(ab')$_2$ FRAGMENTS OF MOUSE ANTI-RAT Ig BOUND TO SURFACE ANTIGEN | | |
|---|---|---|---|---|---|
| | | | THY-1 | LYT-1 | L3T4 |
| P815 | — | — | 600 | 700 | 500 |
| SKK45.10 | — | I-A$^k$ + KLH | 77,000 | 3,000 | 900 |
| F3 | BALB/c | I-E$^d$ + GLT | 70,000 | 14,000 | 7,200 |
| E10 | BALB/c | I-E$^d$ + GLT | 73,000 | 14,000 | 20,000 |
| O3 | BALB/c | I-A$^d$ + OVA | 1,000 | 800 | 13,000 |
| C2 | BALB/c | I-A$^b$ | 65,000 | 11,000 | 6,900 |
| N5 | C57BL/6 | I-A$^b$ + NP-OVA | 77,000 | 12,000 | 20,000 |
| N7 | C57BL/6 | I-A$^b$ + NP-CGG | + | + | + |
| B6 | C57BL/6 | I-A$^d$ | + | + | + |

KLH = keyhole limpet hemocyarin
GLT = random polymer of glutamic acid, lysine, and tyrosine
OVA = ovalbumin
NP-CGG = chicken gamma globulin conjugated with (4-hydroxy-3-nitrophenyl) acetyl.
+ = test positive by FACS The individual antigen specific clones of Table I are derived as described in DeKruyff et al., *J. Immunol.* 136:446 (1986); Clayberger et al., *J. Exp. Med.* 157:1906 (1983); Friedman et al., *J. Exp. Med.* 161:785 (1985); and Rao et al., *Immunogenetics* 17:147 (1983). To determine the phenotype of their cell surface antigens, binding assays were carried out in the following manner: F(ab')$_2$ fragments of mouse anti-rat IgG was radiolabeled with Na$^{125}$I by the chloramine-T method of R. Hunter [*Proc. Soc. Exp. Biol. Med.* 113:987 (1970)]. Labeled antibodies were purified through a Sephadex G-25 Column to remove free $^{125}$I. Subsequently, a million cells of each clone were individually incubated with 10–50 ul of monoclonal antibody specific for Thy-1, Lyt-1, or L3T4 surface antigens in 100 ul of phosphate buffered saline (hereinafter "PBS") containing 10 mg/ml human gamma globulin (hereinafter "HGG") and 1 mg/ml sodium azide. After incubation at room temperature for 45 minutes with frequent shaking, all cells were washed three times with PBS-BSA fluid containing PBS and 5 mg/ml bovine serum albumin (hereinafter "BSA"). The cells were resuspended in 100 ul of PBS-HGG buffer containing 20 ng of $^{125}I$ labeled F(ab')$_2$ mouse anti-rat Ig (approximately 400,000 cpm) and incubated for 45 minutes at room temperature with frequent shaking. The cells were then washed three times with PBS-BSA solution and the bound radiolabeled antibody fragments counted with a Beckman γ-4000 counter.

Experimental Series 2

Initially, the ability of macrophage hybridomas to proliferate in the presence of mitomycin C-treated alloreactive L3T4+ T-cell clones was evaluated. For this purpose, macrophage hybridoma M059, M05, and mastocytoma P815 were utilized. The generation and maintenance of M059 and M05 macrophage hybridomas have been described [Ju and Dorf, J. Immunol. 134:3722 (1985)]. These hybridomas bear the heterozygous H-$2^d$/H-$2^k$ haplotype. The P815 tumor does not express Class II antigen at all. Functionally, the M059 hybridoma expresses high levels of surface I-A$^d$ and I-A$^k$ while surface I-A is undetectable on either the M05 or P815.

B6 (1-A$^d$ alloreactive) T cell clones described earlier in Table I were incubated with 40 ug/ml of mitomycin C (Sigma Chemical Company) for 45 minutes in a 37 C 10% CO$_2$ incubator. After washing three times with DMEM+10% FCS, 6×10$^4$ cells of mitomycin C-treated clone B6 were mixed with 5×10$^3$ viable cells of hybridomas M059, M05, and P815 cells individually in separate wells of a microtiter plate. After incubation in a 37 C, 10% CO$_2$ incubator for 24 hours, each well was pulsed with [$^3$H]-thymidine (1 uCi/0.02 ml). DNA synthesis was then measured after an additional 24 hour incubation period. The results are presented in Table II.

cordingly, the ability to inhibit proliferation of M059 is due to the activation of T-cell clone B6 (as evidenced by the production of lymphokine IL-2) while the M05 and the P815 hybridoma cells fail to activate T-cell clone B6.

Experimental Series 3

To determine whether the failure of hybridoma M059 cells to proliferate in the presence of T cell clone B6 is due to cytostatic growth inhibition or to cytolytic killing, the hybridoma M059 cells were labeled with $^{51}$Cr and the chromium release evaluated at various times after coculture. Initially, one million cells of M059 were incubated with 250 uCi of $^{51}$Cr (New England Nuclear Corporation, Cambridge, Mass.) in DMEM containing 2.5% FCS. After 90 minutes reaction in a 7 C, 10% CO$_2$ incubator, the hybridoma cells were washed three times with DMEM+10% FCS and resuspended in 5.0 ml of DMEM containing 10% FCS. 50 ul aliquots containing 10$^4$ cells labeled with $^{51}$Cr were used in each assay.

In this experiment, the T-cell clone B6 was not pretreated with mitomycin C. Rather, 50 ul of cell suspension containing 0.7–10×10$^4$ clone B6 cells was incubated with 10$^4$, $^{51}$Cr-labeled M059 in 50 ul aliquots individually in microtiter plates. The final volume of mixed culture was always 200 ul. Incubation at 37 C in a 10% CO$^2$ incubator was allowed to proceed for various periods of time and 100 ul of supernatant was collected and counted for the presence of $^{51}$Cr using a Beckman γ-4000 counter. Spontaneous release was calculated as the cpm release from hybridoma cells incubated alone in the medium without clone B6 cells. Cytotoxicity was expressed as percentage specific $^{51}$Cr release according to the formula:

% specific $^{51}$Cr release=100x (cpm of test sample—cpm of spontaneous release)÷(cpm of total release—cpm of spontaneous release).

TABLE II

| TARGET CELL TESTED | T-CELL CLONE | [$^3$H]THYMIDINE INCORPORATION OF TARGETS (CPM) | IL-2 ACTIVITY (CPM) |
|---|---|---|---|
| Ia$^+$M059 | — | 44,000 ± 3,500 | 240 ± 80 |
|  | + | 7,200 ± 480 | 26,000 ± 2,400 |
| Ia$^-$M05 | — | 28,000 ± 1,800 | 540 ± 120 |
|  | + | 24,000 ± 900 | 800 ± 200 |
| Ia$^-$p815 | — | 38,000 ± 2,000 | 300 ± 200 |
|  | + | 39,500 ± 3,100 | 280 ± 150 |

The empirical results indicate that the proliferation of hybridoma M059 (expressing 1-A$^d$) was dramatically reduced in the presence of the T cell clone B6 In contrast, proliferation of hybridomas M05 (undetectable IA expression) or P815 (Ia negative) was not significantly inhibited by the presence of the B6 T-cell clone. In comparison, an irrelevant T cell clone N7 which is 1-A$^b$ restricted and NP-CGG specific (see Table I) did not inhibit M059 proliferation (data not shown). Ac- Cpm of total release is obtained by lysing the $^{51}$Cr labeled target cells with 2.0% Triton-X. In most cases, spontaneous 51Cr release range between 10% and 50%. The results are presented in Table III.

TABLE III

| TIME AFTER COCULTURE (HR) | SPONTANEOUS RELEASE (%) | % SPECIFIC RELEASE (NO. VIABLE CELLS KILLED) | | |
|---|---|---|---|---|
| | | 9 × 10$^4$ EFFECTOR CELLS | 3 × 10$^4$ EFFECTOR CELLS | 1 × 10$^4$ EFFECTOR CELLS |
| 4 | 10 | 0 (0) | 0 (0) | 0 (0) |
| 9 | 29 | 16 (1,136) | 14 (994) | 9 (639) |
| 13 | 35 | 38 (2,470) | 31 (2,015) | 21 (1,365) |
| 18 | 45 | 79 (4,345) | 68 (3,740) | 55 (3,025) |
| 24 | 50 | 100 (5,000) | 95 (4,750) | 80 (4,000) |

The empirical data presented by Table III indicate that the observed growth inhibition is due to the killing of M059 hybridoma cells. Note however, that cytolysis was not observed at the 4 hour interval of cell interaction even with a high effector (B6 clone cell) to target (hybridoma M059) ratio of 9:1. Weak, but significant, killing can be detected at the 9 hour interval of incubation. Maximal cytolysis is observed at the 20-24 hour of incubation. While a high spontaneous release rate is observed in the experiment, the overall conclusion remains that the B6 clone cells express cytolytic activity in accordance with increasing incubation time or with increasing numbers of effector clone B6 cells. Subsequent experiments with several other Ia-bearing M0 hybridomas and T-cell clones also fail to demonstrate $^{51}$Cr release after 4 hours incubation but clearly demonstrate active cytolysis after an incubation period of from 18-20 hours under similar test conditions.

appropriate Ia determinants. In comparison, target cells expressing irrelevant Ia determinants were not significantly lysed. Quantitatively, all 13 different T cell clones tested specifically lysed each APC bearing the appropriate combination of a specific antigen and the Ia determinant.

Experimental Series 5

A series of individual experiments were undertaken to demonstrate that the cytolytic activity expressed by activated inducer T-cells involves recognition and interaction of MHC Class II antigens with T-cell receptor. The substance of the experiments and the empirical results are presented by Table IV below.

TABLE IV

| | | % SPECIFIC RELEASE+ | | | |
|---|---|---|---|---|---|
| EFFECTOR CLONES | TARGET CELLS* | CONTROL | ANTI-I-A$^{b,d}$ | ANTI-L3T4 | KJ16.133 |
| 03(I-A$^d$ + OVA) | Ia$^-$M05(k × d) | 2 | NT | NT | NT |
| | Ia$^+$M05(k × d) | 45 | 0 | 22 | 43 |
| | Ia$^+$M059(k × d) | 41 | 17 | 18 | 42 |
| | Ia$^+$LK(k × d) | 50 | 21 | 20 | 48 |
| N5(I-A$^b$ + NP-OVA) | Ia$^+$M0B64(b × d) | 25 | 4 | 1 | 10 |
| | Ia$^+$LB(b × d) | 41 | NT | 0 | 15 |
| SKK5.10(I-A$^k$ + KLH) | Ia$^+$M059(k × d) | 54 | 50 | 51 | 16 |
| | Ia$^+$LK(k × d) | 63 | 64 | 59 | 18 |

Target cells included M0 hybridomas (5, 59, and B64) and B hybridomas (LK and LB). Letters in parentheses indicate the H-2 haplotypes of the target cells. Ia + M05 and Ia + M0B64 were obtained by treatment with Con A supernatent containing interferon-γ.
+ MAb (50 ul) to I-A$^{b,d}$(M5/114), L3T4 (GK1.5, and a T-cell receptor allotypic determinant (KJ16.133) were added as inhibitors. Spontaneous release from target cells ranged from 30 to 55%.NT, not tested.

Experimental Series 4

To demonstrate that L3T4+ inducer T cell clones generally are able to express cytolytic activity after activation, 13 different L3T4+, nominal antigen-specific, and Ia-restricted or Ia-alloreactive, inducer T-cell clones were tested for expression of cytolytic function. Three major types of antigen-presenting cells were tested as target cells. These included 7 different M0 hybridomas; 3 different B hybridomas; and a dendritic cell line that expresses Ia antigens. Varying numbers of each T cell clone (x10$^4$ cells) were incubated with 1×10$^4$ cells of $^{51}$Cr-labeled chosen target cell in the presence or absence of the appropriate specific antigen (100 ug/ml) in a total of 200 ul as previously described. After 20 hours incubation at 37 C in a 10% CO$_2$ incubator, 100 ul of supernatant was removed from each reaction mixture and counted for presence of radioactive chromium. Representative results are illustrated in FIGS. 1a–1c for T cell clones B6, C2, F3, and N7 respectively. In these experiments, two antigen-specific, Ia-restricted clones (the F3 clone specific to I-E$^d$+GLT antigens and the N7 clone, specific to I-A$^b$+NP-CGG antigens) and two Ia-specific clones (the B6 clone, alloreactive to I-A$^d$ and the C2 clone, alloreactive to I-A$^b$) were used as effectors. The respective $^{51}$Cr-labeled target cells were: in FIG. 1a, Ia$^k$/Ia$^d$-bearing M059 cells; in FIG. 1b, Ia$^k$/Ia$^d$-bearing B hybridoma LK cells; and in FIG. 1c, a dendritic cell line (Den-I) that expresses IA$^b$. As illustrated by FIG. 1 generally, after the 20 hour incubation period (of the respective T-cell clones with the appropriate combination of nominal exogenous antigen and Ia-bearing target cells) essentially complete release of $^{51}$Cr was observed in each instance. Furthermore, ir those experiments conducted in the absence of specific antigen, $^{51}$Cr release from the respective target cells remained at background levels. In a similar fashion, alloreactive T-cell clones specifically lysed their target cells bearing the First, a macrophage hybridoma, M05, which does not constitutively express I-A$^d$ antigen is not lysed by an OVA-specific I-A$^d$ restricted T cell clone (clone 03). However, if the M05 macrophage hybridoma were pretreated with gamma interferon to specifically induce I-A$^d$ expression, clone 03 effectively killed the Class II antigen bearing M05 hybridoma in the presence of a specific antigen. Second, the specific killing of the Ia+ M05, M0-59, M0B64, LK, and LB antigen presenting cells respectively is significantly inhibited with the addition into the reaction mixture of a monoclonal antibody (M5/114) reactive against the I-A$^d$ and I-A$^b$ determinants. It is significant to note that lysis of I-A$^k$-bearing target cells (M059 and Lk cells) by the T-cell hybridoma SKK45.10 was not affected or inhibited by this specific antibody (which does not react with the I-A$^k$ determinant). Finally, the addition of either a monoclonal antibody specific for T cell receptor (KJ16.133) or a monoclonal antibody specific against the L3T4 molecule (GK1.5) each inhibited the killing of the target APC. The inhibition of cytolysis by the KJ16.133 antibody correlates directly with the expression of this determinant of the T cell clones utilized (see Table I). Thus, the killing of the target APC by the T-cell clone N5 or the T-cell hybridoma SKK45.10, each of which bears this determinant, was substantially inhibited. In contrast, the addition of the monoclonal antibody KJ16.133 did not affect the cytolysis of the target APC by T-cell clone 03 which lack this determinant. Similarly, the monoclonal antibody GK1.5 inhibited killing by T-cell clones N5 and 03 that express the L3T4 determinant on their cell surfaces. In contrast, however, the monoclonal antibody GK1.5 did not prevent APC lysis by the T-cell hybridoma SKK45.10 which lacks surface L3T4 molecules (see Table I). It is clear, therefore, that the presence of the Class II antigen on the target APC cell is required; and that the observed cytolysis is the direct result of activating the inducer T-cells through the interaction of T-cell receptor and the antigen-Ia complex.

Experimental Series 6

To demonstrate the inhibition of localized tumor growth in-vivo using the present invention, the following protocol was employed. 25 individual BALB/c mice were divided into 9 individual groups, each mouse being subjected to 300 rads of irradiation. Each group of mice, containing from 2-4 members, then received a subcutaneous injection of B lymphoma A20.2J, ($40 \times 10^6$ cells) alone or in combination with varying concentrations ($1.3$–$4.0 \times 10^6$ cells) of T-cell clone 03. After waiting 20 minutes, each animal received a second subcutaneous injection of either phosphate buffered saline (PBS) or of ovalbumin (2.0 mg) in PBS near the site of the transferred tumor cells. At regular intervals of 3-4 days (approximately twice per week) each group of mice received either additional subcutaneous injections of saline or ovalbumin antigen solutions. The repetition of antigen or saline injection continued for a period to of 15 calendar days. No further treatment was given any of the mice after the fifteenth day of experiment, except for group 9. The mice of group 9 continued to receive the periodic injections of ovalbumin solution through the experiment. Each mouse was followed individually and by group to determine the size of tumor grown (by two perpendicular measurements) and by the numbers of mouse deaths. The empirical data is presented in Table V below.

TABLE V

| GROUP | NUMBER TESTED | T CELL O₃ CLONE TRANSFERRED | A20.2J TUMOR CELLS TRANSFERRED | TREATMENT OVA OR PBS (1 mg/3 D) | \multicolumn{4}{TUMOR GROWTH (CM²) Test DAY (D)} | \multicolumn{10}{MORTALITY TEST DAY (d)} |
|---|---|---|---|---|---|---|---|---|---|---|---|---|---|---|---|---|---|---|
| | | | | | D11 | D21 | D36 | D39 | D41 | D42 | D46 | D47 | D48 | D52 | D60 | D61 | D64 | D69 | D76 |
| 1 | 3 | $12 \times 10^6$ | $40 \times 10^6$ | PBS | 1.44 | 3.06 | 9.52 | 1 | | | | | | | | | | | |
| | | | | | 1.0 | 4.0 | d | 1 | | | | d | | | | | | | |
| | | | | | 1.1 | 2.24 | 8.32 | 1 | | | | | | | | | | | |
| 2 | 3 | $12 \times 10^6$ | $40 \times 10^6$ | OVA | 0 | 0 | 0 | 1 | | | | | | | | | | d | |
| | | | | | 0 | 0 | 0.48 | 1 | | | | | | d | | | | | |
| | | | | | 0 | 0 | 0 | 1 | | | | | | | | | | | d |
| 3 | 2 | $4 \times 10^6$ | $40 \times 10^6$ | PBS | 1.56 | 5.06 | 13.6 | 1 | d | | | | | | | | | | |
| | | | | | 1.68 | 4.4 | 12.16 | 1 | | | | d | | | | | | | |
| 4 | 2 | $4 \times 10^6$ | $40 \times 10^6$ | OVA | 0 | 0 | 0 | 1 | | | | | | | d | | | | |
| | | | | | 0 | 0 | 4.08 | 1 | | | d | | | | | | | | |
| 5 | 2 | $1.33 \times 10^6$ | $40 \times 10^6$ | PBS | 1.68 | 4.62 | 11.88 | 1 | d | | | | | | | | | | |
| | | | | | 1.69 | 3.74 | 9.60 | 1 | | | | d | | | | | | | |
| 6 | 2 | $1.33 \times 10^6$ | $40 \times 10^6$ | OVA | 0 | 1.68 | 5.5 | 1 | | | | | | d | | | | | |
| | | | | | 0 | 0.63 | 0.3 | 1 | | | | | | | | d | | | |
| 7 | 4 | 0 | $40 \times 10^6$ | PBS | 1.96 | 4.60 | 14.43 | 1 | d | | | | | | | | | | |
| | | | | | 0.96 | 3.78 | 15.4 | 1 | | d | | | | | | | | | |
| | | | | | 1.68 | 5.06 | 11.47 | 1 | | | | | d | | | | | | |
| | | | | | 1.1 | 3.6 | 13.80 | 1 | | | | | d | | | | | | |
| 8 | 4 | 0 | $40 \times 10^6$ | OVA | 1.56 | 4.0 | 10.88 | d | d | | | | | | | | | | |
| | | | | | 1.1 | 3.6 | 9.60 | d | | | | d | | | | | | | |
| | | | | | 1.44 | 3.06 | 9.00 | 1 | | | | | d | | | | | | |
| | | | | | 0.84 | 3.23 | 9.8 | 1 | | | | | | | d | | | | |
| 9 | 2 | $14 \times 10^6$ | $40 \times 10^6$ | OVA | 0 | 0 | 0 | 1(0) | | | | | | | | | | | 1(0) |
| | | | | | 0 | 0 | 0 | 1(0) | | | | | | | | | | | 1(0) |

PBS = phosphate buffered saline
OVA = ovalbumin
1 = live
d = diseased, tumor in gross
1 (0) = live, normal with no visible tumor mass As is readily apparent by FIG. 2a, those individual mice and those respective groups of mice receiving the age of tumor positive containing wells calculated. The results are presented in Table VI below.

TABLE VI

| 36 HOUR OBSERVATION INDIVIDUAL MICE/ RANDOMLY SELECTED WELLS | NUMBER OF TUMOR COLONIES/WELL | | | | | |
|---|---|---|---|---|---|---|
| | E10 CLONE TREATED | | | CONTROL | | |
| | 1 | 2 | 3 | 4 | 5 | 6 |
| 1 | 0 | 0 | 0 | 6 | 5 | 14 |
| 2 | 0 | 0 | 0 | 11 | 10 | 8 |
| 3 | 0 | 0 | 0 | 11 | 6 | 7 |
| 4 | 0 | 0 | 0 | 18 | 9 | 18 |
| 5 | 0 | 0 | 0 | 16 | 7 | 18 |
| 6 | 0 | 0 | 0 | 14 | 7 | 8 |
| 7 | 0 | 0 | 0 | 7 | 6 | 15 |
| 8 | 0 | 0 | 0 | 8 | 7 | 14 |
| 9 | 0 | 0 | 0 | 13 | 11 | 20 |
| 10 | 0 | 0 | 0 | 16 | 12 | 9 |
| Percent Positive Wells d2 | 0 | 0 | 0 | 100 | 100 | 100 |
| Percent Positive Wells d4 | 0 | 0 | 6 | 100 | 100 | 100 |
| Percent Positive Wells d7 | 0 | 0 | 6 | 100 | 100 | 100 | d = days after culture in-vitro

T-cell clone 03 and injections of ovalbumin revealed no tumor growth as long as specific antigen was administered periodically. In comparison, those individual mice and those mouse groups receiving only saline quickly demonstrated tumor growth in gross as illustrated by FIG. 2b. Cessation of antigen administration resulted in tumor development. It is especially noteworthy, however, that the onset of tumor growth was substantially delayed for mice receiving specific antigen. In addition, when large numbers of 03 cells were used, the life span of such mice was significantly prolonged. Finally, it should be recognized that 2 mice that periodically received antigen injections throughout the experimental period never developed tumors at all and remain alive to date (group 9).

Experimental Series 7

To demonstrate the ability of the present invention to inhibit systemic tumor growth in in-vivo, the following experimental protocol was followed: two groups of mice containing three members each were irradiated with 300 rads and received $30 \times 10^6$ cells of the B lymphoma cell A20.2J by intravenous injection. One group of test mice also received $5 \times 10^6$ cells of the T cell clone E10 having a nominal antigenic specificity for the GLT antigen (Table I). The second group comprising controls received an injection of saline only. Subsequently, approximately ½ hour after the administration of the tumor cells, 2.0 mg of GLT antigen was given intraperitoneally to each mouse in both groups. Additional injections of 2.0 mg of antigen were given to each mouse every third day in sequence thereafter for the duration of the test period. On the seventh day of the testing period, the three members of the group receiving clone E10 cells received a booster injection of $5 \times 10^6$ E10 cells. At the fourteenth day in the testing period, all the animals were sacrified and their individual spleens removed by dissection. Subsequently, $5 \times 10^2$ spleen cells from each animal were placed in individual wells of a microtiter plate and cultured in DMEM +10% FCS in a 37 C, 10% $CO_2$ incubator. The numbers of tumor colonies per well were counted after 36 hours of incubation. The individual wells were reexamined at four days and seven days incubation time as well and the percent- The present invention is not to be restricted in form nor limited in scope except by the claims appended hereto.

What I claim is:

1. An in-vivo method for therapeutically treating a living subject afflicted with abnormal cells which express a major histocompatibility complex Class II antigen, said method comprising the steps of:
   administering a plurality of non-activated inducer T-cell lymphocytes to the living subject, said non-activated inducer T-cell lymphocytes having a demonstratable specificity for another antigen in addition to a major histocompatibility Class II antigen;
   introducing said other antigen to the abnormal cells within the subject at a desired time such that the abnormal cells take up said introduced other antigen and act in-vivo as antigen-presenting cells;
   allowing said administered T-cell lymphocytes to become activated in-vivo by said introduced other antigen; and
   waiting for said in-vivo activated inducer T-cell lymphocytes to express cytolytic activity against said antigen-presenting cells comprising the abnormal cells in the living subject.

2. An in-vivo method for therapeutically treating a living subject afflicted with tumor cells which express a major histocompatibility complex Class II antigen, said method comprising the steps of:
   administering a plurality of non-activated inducer T-cell lymphocytes to the living subject, said non-activated inducer T-cell lymphocytes having a demonstratable specificity for an exogenous antigen in addition to a major histocompatibility Class II antigen;
   introducing said exogenous antigen to the tumor cells within the subject at a desired time such that the tumor cells take up said introduced exogenous antigen and act in-vivo as antigen-presenting cells;
   allowing said administered T-cell lymphocytes to become activated in-vivo by said introduced exogenous antigen; and
   waiting for said in-vivo activated inducer T-cell lymphocytes to express cytolytic activity against said antigen-presenting cells comprising the tumor cells in the living subject.

3. The method as recited in claim 1 or 2 wherein said inducer T-cell lymphocytes comprise cloned T-cells.

4. The method as recited in claim 3 wherein said cloned inducer T-cell lymphocytes are derived from the T-cells of the afflicted subject.

5. The method as recited in claim 1 or 2 wherein the major histocompatablity complex Class II antigen of said cells is constitutively expressed 6. The method as recited in claim 1 or 2 wherein the major histocompatability complex Class II antigen of said cells is inductively expressed.

7. The method as recitedin claim 1 or 2 wherein said inducer T-cell lymphocytes administered to the subject are syngeneic.

* * * * *